(12) United States Patent
Smith (10) Patent No.: US 9,128,085 B2
(45) Date of Patent: Sep. 8, 2015

(54) RAPID TEST FOR GLYCATED ALBUMIN IN BLOOD

(75) Inventor: Henry John Smith, Temecula, CA (US)

(73) Assignee: Epinex Diagnostics, Inc., Tustin, CA (US)

( * ) Notice: Subject to any disclaimer, the term of this patent is extended or adjusted under 35 U.S.C. 154(b) by 702 days.

(21) Appl. No.: 12/480,091

(22) Filed: Jun. 8, 2009

(65) Prior Publication Data

US 2009/0246801 A1   Oct. 1, 2009

Related U.S. Application Data

(63) Continuation of application No. 11/474,561, filed on Jun. 27, 2006, now abandoned.

(60) Provisional application No. 60/699,595, filed on Jul. 18, 2005.

(51) Int. Cl.
  *G01N 33/558* (2006.01)
  *G01N 33/543* (2006.01)
  *G01N 33/68* (2006.01)

(52) U.S. Cl.
  CPC ........ *G01N 33/558* (2013.01); *G01N 33/54386* (2013.01); *G01N 33/6893* (2013.01); *G01N 2333/76* (2013.01)

(58) Field of Classification Search
  USPC .......... 435/4, 7.1, 287.1, 287.2, 287.7, 287.9, 435/188.7; 436/501, 514, 518, 528, 164, 436/166, 169, 172, 807
  See application file for complete search history.

(56) References Cited

U.S. PATENT DOCUMENTS

| | | | |
|---|---|---|---|
| 5,110,745 A | 5/1992 | Kricka et al. |
| 5,223,392 A | 6/1993 | Cohen |
| 5,506,144 A | 4/1996 | Sundrehagen |
| 5,656,448 A | 8/1997 | Kang et al. |
| 5,821,073 A | 10/1998 | Lee |
| 5,821,399 A | 10/1998 | Zelin |
| 5,919,708 A | 7/1999 | Sundrehagen |

(Continued)

FOREIGN PATENT DOCUMENTS

| | | |
|---|---|---|
| EP | 0455225 | 11/1991 |
| EP | 0769697 | 4/1997 |

(Continued)

*Primary Examiner* — Chris L Chin
(74) *Attorney, Agent, or Firm* — K&L Gates LLP; Louis C. Cullman; Michelle Glasky Bergman (57) ABSTRACT

This invention describes a rapid assay for measuring the ratio of glycated albumin to total albumin in blood. Patients with diabetes have elevated levels of glucose in their blood that can react with plasma albumin to form glycated albumin. The amount of glycated albumin formed is directly correlated with the level of plasma glucose that the albumin has been exposed to over a period of time. The ratio of glycated albumin to total albumin in blood will provide an indication of the average amount of protein glycation that occurred over the preceding 2-3 week period.

The test is performed using a disposable strip or cassette that contains the testing reagents and the results are measured in a measuring instrument that automatically reads, calculates and displays the final result. The results of tests performed over a period of time are stored in the instrument's memory and presented in a numerical or graphical format so that the individual's glycated albumin level can be monitored over time.

11 Claims, 5 Drawing Sheets

Overhead view of Test Strip.

(56) References Cited

U.S. PATENT DOCUMENTS

| | | |
|---|---|---|
| 6,670,115 B1 | 12/2003 | Zhang |
| 6,670,192 B1 | 12/2003 | Galen et al. |
| 7,195,923 B2 * | 3/2007 | McCroskey et al. ............ 436/87 |
| 2002/0146754 A1 | 10/2002 | Kitawaki et al. |
| 2002/0164811 A1 | 11/2002 | Hud et al. |
| 2003/0068830 A1 | 4/2003 | McCroskey et al. |
| 2003/0170881 A1 | 9/2003 | Davis |
| 2004/0265941 A1 | 12/2004 | Galen et al. |
| 2006/0148096 A1 | 7/2006 | Jina |
| 2006/0223192 A1 | 10/2006 | Smith et al. |
| 2006/0270060 A1 | 11/2006 | Smith |
| 2007/0015291 A1 * | 1/2007 | Smith ........................... 436/514 |

FOREIGN PATENT DOCUMENTS

| | | |
|---|---|---|
| JP | 2001-133457 | 5/2001 |
| WO | 02/33414 | 4/2002 |
| WO | 2005/031356 | 4/2005 |

* cited by examiner

Figure 1. Overhead view of Test Strip.

Figure 2. Fluorometer Instrument (10)

Figure 3. Spectrophotometer Instrument (24)

Figure 4 a. Biosensor cassette (38) enlarged.

Figure4b. Biosensor Instrument (39)

RAPID TEST FOR GLYCATED ALBUMIN IN BLOOD

CROSS-REFERENCE TO RELATED APPLICATIONS

The following patent application is a continuation of U.S. patent application Ser. No. 11/474,561 filed on Jun. 27, 2006 now abandoned, entitled RAPID TEST FOR GLYCATED ALBUMIN IN BLOOD, the teachings of which are incorporated herein by reference.

The present application is a non-provisional application claiming priority to U.S. Provisional Patent Application Ser. No. 60/699,595 entitled RAPID TEST FOR GLYCATED ALBUMIN IN BLOOD, filed Jul. 18, 2005.

FEDERALLY SPONSORED RESEARCH OR DEVELOPMENT

None

BACKGROUND OF THE INVENTION

Diabetes mellitus or diabetes is a disease characterized by elevated levels of plasma glucose. Uncontrolled hyperglycemia is associated with increased risk of vascular disease including, nephropathy, neuropathy, retinopathy, hypertension, and death. There are two major forms of diabetes. Type 1 diabetes (or insulin-dependent diabetes) and Type 2 diabetes (or noninsulin-dependent diabetes). The American Diabetes Association has estimated that approximately 6% of the world population has diabetes.

The goal of diabetic therapy is to maintain a normal level of glucose in the blood. The American Diabetic Association has recommended that diabetics monitor their blood glucose level at least three times a day in order to adjust their insulin dosages and/or their eating habits and exercise regimen. However, glucose tests can only measure a point in time result and does not provide an overall assessment of glycemic control over a period of time.

To assess glycemic control over an extended period of time it is also recommended that hemoglobin A1c (glycated hemoglobin) testing be done 2-4 times a year. When blood proteins including hemoglobin are exposed to glucose over a period of time they become glycosylated and the degree of glycosylation is dependent on the average concentration of glucose and the length of time the proteins were exposed to the glucose. The level of glycated hemoglobin is also dependent upon the half-life of the hemoglobin molecule within the body. The net result is that measurement of glycated hemoglobin provides an estimate of the degree of glycosylation that occurred over the preceding 2-3 months.

It would be desirable to have a test that would provide an earlier indication of glycemic control to allow earlier therapeutic intervention. There are currently several procedures available for measuring glycemic control over a shorter period of time. The fructosamine test measures the amount of glycated proteins in blood; and there is also an enzymelinked immunoassay (ELISA) for measuring glycated and total albumin in a blood sample. These tests are performed by skilled technical staff in a laboratory setting.

It would also be desirable to develop a simplified point-of-care assay that could be utilized in a point-of-care setting such as the doctor's office or by the patient at home.

BRIEF SUMMARY OF THE INVENTION

This invention describes a rapid test method of measuring glycated albumin compared to total albumin using a blood sample. As the half-life of albumin in blood is approx. 17 days the result provides an assessment of glycemic control over the preceding 2-3 weeks. In this invention the term blood sample includes the use of whole blood, and/or the plasma fraction and/or the serum fraction.

Frequent monitoring of the individuals glycated albumin would provide an accurate assessment of overall effectiveness of glycemic control in the individual and allow earlier therapeutic intervention compared to the glycated hemoglobin test in current use.

The present invention describes a simplified point-of-care assay that utilizes disposable test strips or cassettes and a reusable measuring instrument.

DESCRIPTION OF THE INVENTION

This invention describes a procedure for measuring the percent of glycated albumin compared to total albumin in the patient's blood. The patient's blood sample is placed in a test cassette that contains reagents to perform the test. The test cassette is then inserted into a measuring instrument that reads, calculates, stores and reports the result.

Principle: The Rapid Assay for glycated albumin utilizes antibodies to glycated albumin and antibodies to total albumin.

Figure 1:
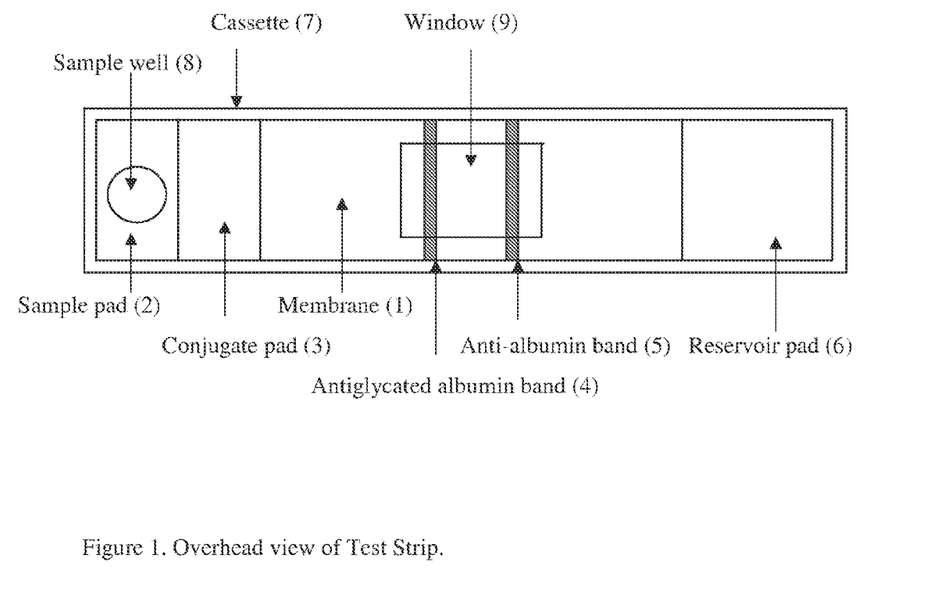
FIG. 1. is an illustration of the lateral flow disposable test strip containing the reagents and the placement of the components required to measure glycated and non-glycated albumin.

Components for Lateral Flow Devices:

The test strip for measuring glycated albumin is shown in FIG. 1. It consists of a cellulose nitrate membrane (1) or similar membrane support. There is a sample application pad (2) that serves to remove particulate material and allow the fluid component to flow through. Distal to the sample application pad there is band of anti-albumin antibody labeled with an indicator agent (3). Further along the membrane there is a band of anti-glycated albumin antibody (4) fixed to the membrane; and further along the membrane there is a band of anti-albumin antibody (5) fixed to the membrane; and further along the membrane there is a reservoir pad (6) at the distal end of the membrane. The test strip is enclosed within a rigid cassette (7) containing a sample well (8) and window segments (9) to allow for measurement of the test result using a measuring instrument such as a fluorometer or spectrometer or other applicable instrumentation.

Figure 2:
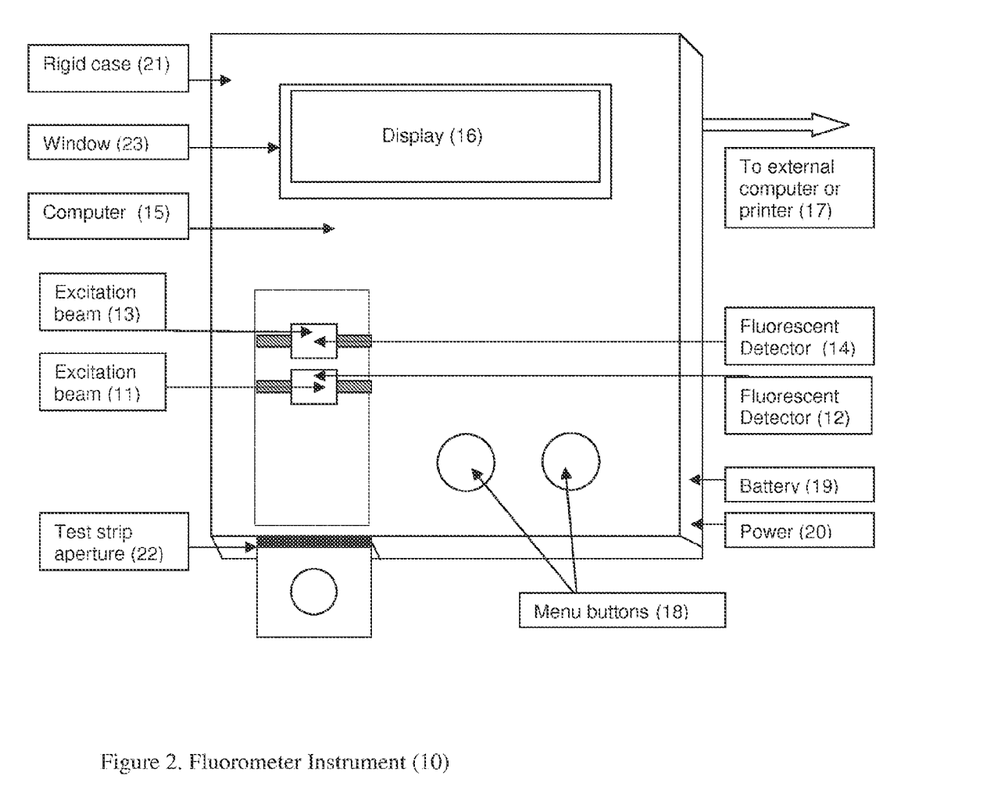
FIG. 2. is an illustration of a fluorescence measuring instrument into which the test strip is inserted. The indicator agent used in the test strip is a fluorescing compound and the amount of fluorescence measured at the glycated albumin band region and at the non-glycated albumin band region is used to calculate the ratio of glycated albumin to total albumin in the sample.

All the measuring instruments share the same basic design. In the fluorometer (10) there is an excitation beam of light emitter (11) at the glycated albumin band with its corresponding fluorescence detector (12); and another excitation beam of light emitter (13) at the non-glycated albumin band with its corresponding fluorescence detector (14). The intensity of fluorescence from each band is measured and used to calculate the result. There is an on-board computer (15) that performs the calculations and reports the result, which is displayed on a liquid crystal display (16) or sent to an external computer or printer (17). Commands to the computer are made via a set of keys or menu buttons (18). The instrument is powered by a battery (19) or external power source (20). The external case is made of a rigid material (21) with an aperture (22) for insertion of the test cassette and a window (23) for the LCD.

Figure 3:
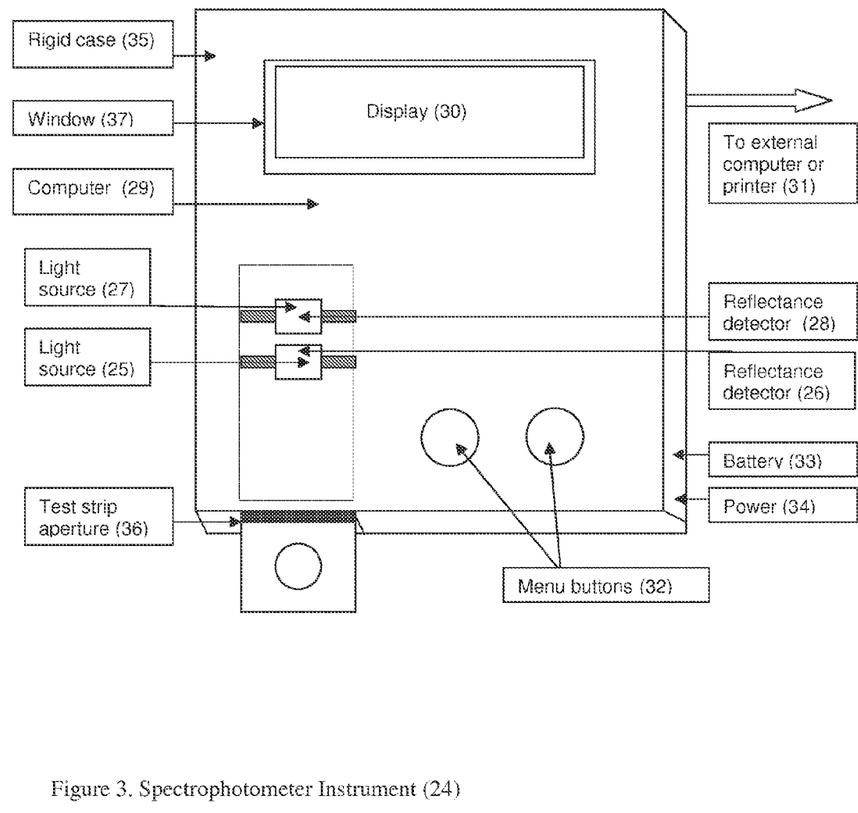
FIG. 3. is an illustration of a spectrophotometer measuring instrument into which the test strip is inserted. The indicator agent used in the test strip is a colored compound or microparticle such as colloidal gold and the color intensity measured at the glycated albumin band region and at the non-glycated albumin band region is used to calculate the ratio of glycated albumin to total albumin in the sample.

The spectrometer (24) used for measuring the intensity of color has a light source (25) to illuminate the glycated albumin band and a corresponding detector (26) to measure the color intensity of the glycated albumin band. There is a light source (27) to illuminate the non-glycated albumin band with its corresponding detector (28) to measure the color intensity of the non-glycated albumin band. The color intensity from each band is measured and used to calculate the result. There is an on-board computer (29) that performs the calculations and reports the result, which is displayed on a liquid crystal display (30) or sent to an external computer or printer (31). Commands to the computer are made via a set of keys or menu buttons (32). The instrument is powered by a battery (33) or external power source (34). The external case is made of a rigid material (35) with an aperture (36) for insertion of the test cassette and a window (37) for the LCD. Components for biosensor devices.

Figure 4A:
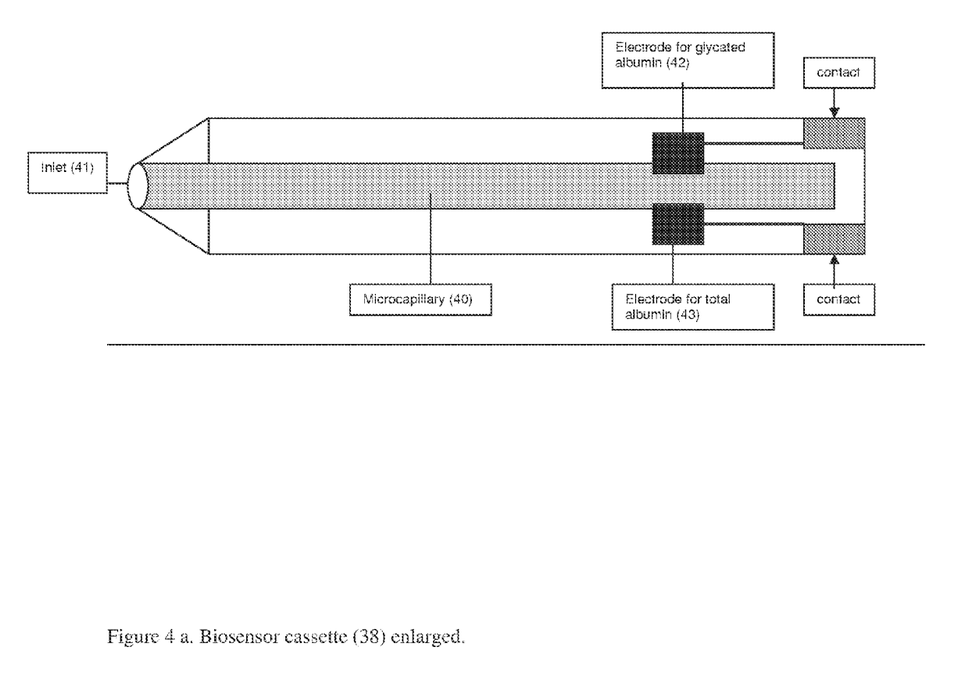
FIG. 4a. is an illustration of the disposable test cassette containing the reagents and the placement of the components required to measure glycated and non-glycated albumin using a biosensor instrument.
Figure 4B:
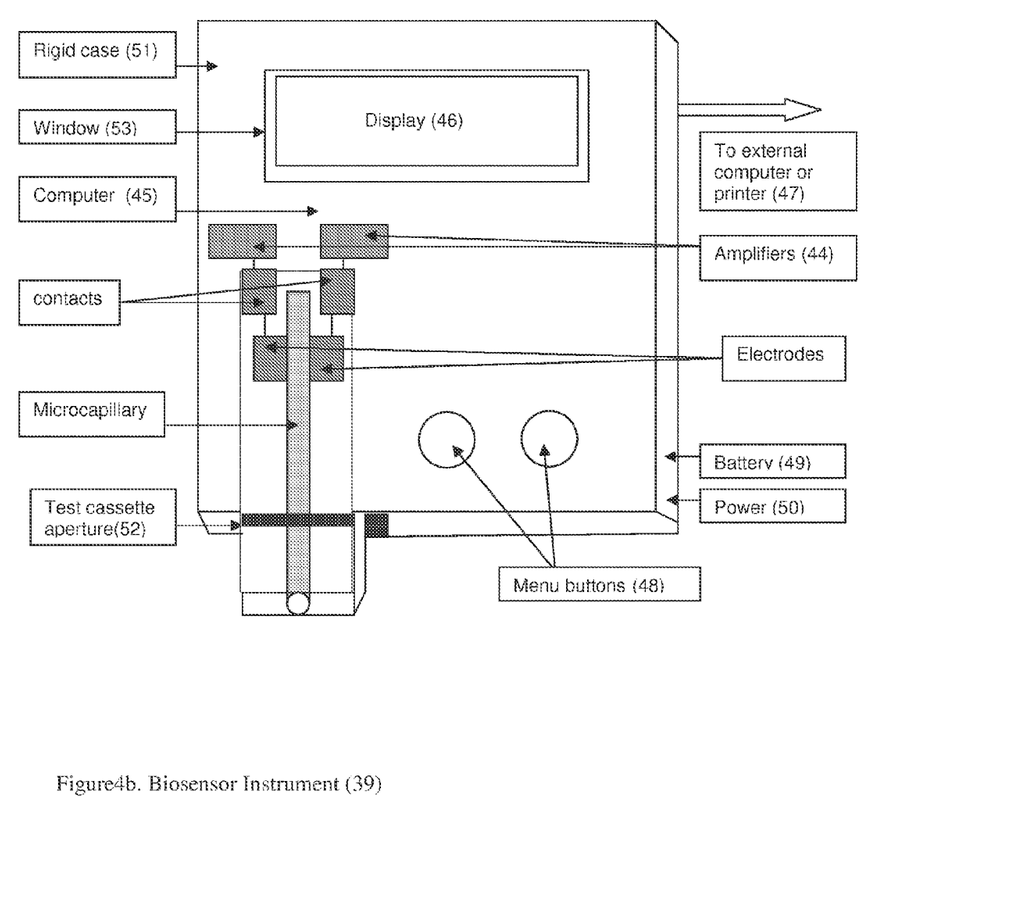
FIG. 4b. is an illustration of a biosensor measuring instrument into which the test cassette is inserted. The indicator agent used in the test cassette is the intensity of the electrical signal generated when the glycated albumin in the sample binds to an anti-glycated albumin antibody coated electrode compared to the signal intensity generated by albumin in the sample binds to its respective anti-albumin antibody coated electrode.

The biosensor cassette (FIG. 4a. 38) and instrument (FIG. 4b. 39) differs from the lateral flow devices in that the sensor cassette contains a microcapillary (40) with an inlet (41) to permit entry of the blood sample. Within the capillary are two electrodes. One electrode is coated with antibody to glycated albumin (42) and the other electrode is coated with antibody to albumin (43). The biosensor instrument includes an amplifier (44) to amplify the electrical signals received from each electrode in the biosensor cassette. The electrical intensity from each electrode is measured and used to calculate the result. There is an on-board computer (45) that performs the calculations and reports the result, which is displayed on a liquid crystal display (46) or sent to an external computer or printer (47). Commands to the computer are made via a set of keys or menu buttons (48). The instrument is powered by a battery (49) or external power source (50). The external case is made of a rigid material (51) with an aperture (52) for insertion of the test cassette and a window (53) for the LCD.

Other types of measuring instruments may be similarly employed and are within the scope of this invention.
Description of the Test Procedure for Lateral Flow Devices:

A blood sample is placed in the sample well and allowed to absorb into the sample application pad. The sample application has a porosity that will filter out particulate material and allow the filtrate to flow through.

The blood sample then migrates along the membrane and mixes with the labeled anti-albumin antibody reagent. The reagent may be a fluorescent dye, or colored compound or colloidal gold or latex microparticles. The labeled reagent binds to the albumin present in the sample and the resultant immune complex migrates along the membrane until it contacts the band of fixed anti-glycated albumin antibody. The anti-glycated albumin antibody will bind and fix any immune complex containing glycated albumin and in turn the indicator reagent moiety of the immune complex also becomes fixed. The remaining immune complexes that do not contain glycated albumin are not bound and continue to migrate along the membrane until they contact the band of fixed anti-albumin antibody. The anti-albumin antibody will bind and fix the immune complexes containing albumin and in turn the indicator reagent also is fixed to the membrane.

The intensity of the glycated albumin band and the non-glycated albumin band are measured in a measuring instrument. The measuring instrument used will depend upon the type of indicator that was used to label the albumin. For example, if a fluorescein label is used then the measuring instrument is a fluorometer designed for this purpose; or if an colored label is used then the measuring instrument is a spectrometer designed for this purpose, or if colloidal gold or latex particles are used then the measuring instrument may be a reflectance spectrophotometer; or if binding to an electrode is involved then the measuring instrument is a biosensor reader.
Description of the Test Procedure for Biosensor Devices;

The inlet orifice of the biosensor cassette is applied to a blood sample and a small amount of the blood is drawn into the microcapillary. The blood sample is filtered through a device that retains the red cells and allows passage of the plasma. The test cassette is introduced into the measuring instrument where the electrodes come into contact with the measuring instrument and the signals are transmitted to the instrument. As the plasma migrates along the capillary the plasma contacts the electrode coated with anti-glycated albumin antibody where the glycated albumin in the sample binds to the electrode and evokes an electrical signal. The plasma also comes into contact with the anti-albumin antibody coated electrode where the albumin in the sample binds to the electrode and evokes an electrical signal.

The intensity of the electrical generated by each electrode is standardized to be proportional to the amount of glycated albumin and total albumin present in the blood sample.
Measurement of Glycated Albumin to Total Albumin;

The intensity of the signals generated by the different types of indicator agents are each measured by their respective reading instruments. Each instrument however, performs the same mathematical algorithm based on the formula:
Percentage ratio of glycated albumin compared to total albumin is $$\frac{A \times 100}{(A + B)}$$

where A is the glycated albumin band and band B is the non-glycated albumin band.

The result is expressed as the percent of glycated albumin to total albumin and displayed on the instrument's display screen.

To monitor diabetic control the test is performed on a periodic basis and the results of successive testing are stored in the measuring instrument's memory. The results can be expressed as a numerical display and/or in a graphical format so that trend analysis of glycemic control over time can be performed. The results can also be sent to an external computer and/or printer for further storage and display.

Materials:

The materials for this assay can produced according to standard laboratory methods or purchased commercially. The membrane employed is a cellulose nitrate membrane or similar porous membrane.

The anti-albumin antibodies are prepared in immunized animals such as rabbits, sheep, goats, or other immunized species of animals, or by monoclonal antibody techniques. Either the whole antiserum, or the IgG purified fraction, or the affinity purified antibody to albumin, or the binding fragments (F ab or F ab2) of the antibody, may be employed. The methods for immunization of animals and the preparation and purification of antibody is performed according to standard laboratory procedures and known to those skilled in the art.

The anti-albumin antibody is labeled with fluorescein or a colored compound according to standard laboratory techniques that are familiar to those skilled in the art. For example, to label the antibody with fluorescein the antibody is mixed with fluorescein isothiocyanate and allowed to react. The fluorescein labeled antibody is then separated from free fluorescein using dialysis, gel-filtration or chromatography techniques.

Alternatively, the anti-albumin antibody may be used to coat colloidal gold particles or colored latex beads. The colloidal gold particles and latex particles are selected to have a diameter size of either 5 nm or 10 nm or 20 nm or 40 nm or some integral diameter within this size range of 5 nm to 50 nm.

Alternatively, in the biosensor assay the anti-albumin antibody can be labeled with an compound that enhances the electrical signal when binding to the electrode occurs. There is also the possibility that the biosensor assay can be made sensitive enough so that an enhancing indicator label is not required and the direct binding of the glycated albumin and total albumin in the sample to their respective electrodes generate and electrical signal of sufficient strength to be measured.

These and other indicator labels for labeling the anti-albumin antibody are known to those skilled in the art and are within the scope of this invention.

The anti-glycated albumin antibodies are prepared in immunized animals such as rabbits, sheep, goats, or other immunized species of animals, or by monoclonal antibody techniques. Either the whole antiserum, or the IgG purified fraction, or the affinity purified antibody to albumin, or the binding fragments (F ab or F ab2) of the antibody, may be employed. The methods for preparing monoclonal antibody and the preparation and purification of antibody is performed according to standard laboratory procedures and known to those skilled in the art.

The anti-glycated antibodies are diluted in a suitable coating buffer and applied as a band across the membrane and become fixed to the membrane upon drying or further treatment. These methods are known to those skilled in the art and are within the scope of this invention.

Alternatively, instead of using anti-glycated antibody it is possible to replace the antibody with chemicals known to bind glycated proteins such as phenyl boronic acids. The phenyl boronic acid is applied as a band to the membrane strip and will become fixed to the membrane upon drying or further treatment. These methods are known to those skilled in the art and are within the scope of this invention.

The anti-albumin antibodies used for binding to the membrane are prepared in immunized animals such as rabbits, sheep, goats, or other immunized species of animals, or by monoclonal antibody techniques. Either the whole antiserum, or the IgG purified fraction, or the affinity purified antibody to albumin, or the binding fragments (F ab or F ab2) of the antibody, may be employed. The methods for immunization of animals and the preparation and purification of antibody is performed according to standard laboratory procedures and known to those skilled in the art.

In the preferred embodiment of this invention monoclonal anti-albumin antibodies are used to be labeled with the indicator reagent and polyclonal antibodies anti-albumin antibodies are used to prepare the fixed band to the membrane.

The general process for preparing rapid immunochromatographic lateral flow assays are employed in this invention. These methods are known to those skilled in the art and do not affect the novelty of this invention which describes a rapid method for assessing glycemic control by measuring the ratio of glycated albumin to total albumin in a blood sample.

The same active ingredients that are used for the lateral flow tests can also be used for the biosensor test. For example, anti-glycated albumin antibodies are used to coat one biosensor electrode and anti-albumin antibodies are used to coat the other biosensor electrode. The antibodies may be polyclonal or monoclonal types. The antibodies may consist of the complete antibody molecule and/or be composed of the binding fragments (F ab or F ab2) of the antibody molecule. The general process for preparing rapid biosensor assays are known to those skilled in the art and do not affect the novelty of this invention which describes a rapid method for assessing glycemic control by measuring the ratio of glycated albumin to total albumin in a blood sample.

What is claimed is:

1. An immunochromatographic method for determining a ratio of glycated albumin to total albumin in at least one blood sample from a patient, the method comprising:
    applying a blood sample to a single test strip, wherein the single test strip comprises:
        (1) a reservoir containing labeled anti-albumin antibody, wherein glycated albumin and albumin present in the sample bind the labeled anti-albumin antibody to form glycated albumin immune complexes and albumin immune complexes;
        (2) anti-glycated albumin antibody or phenyl boronic acid immobilized as a first band on the test strip for measurement of glycated albumin, wherein the first band is distal to a sample well, and the glycated albumin immune complexes bind to the anti-glycated albumin antibody or the phenyl boronic acid; and
        (3) anti-albumin antibody immobilized as a second band on the test strip for measurement of non-glycated albumin, wherein the second band is distal to the first band, and the albumin immune complexes bind to the anti-albumin antibody;
    inserting the test strip into a measuring instrument, wherein the test strip and the measuring instrument measure both glycated albumin and non-glycated albumin directly in the sample; and
    determining the ratio of glycated albumin to total albumin in the sample.

2. A biosensor method for determining a ratio of glycated albumin to total albumin in at least one blood sample from a patient, the method comprising:
    applying a blood sample to a biosensor cassette, wherein the biosensor cassette comprises:
        (1) a microcapillary tube comprising an inlet for application of the sample, (2) an anti-glycated albumin antibody-coated electrode for capture of glycated albumin; and (3) an anti-albumin antibody-coated electrode for capture of albumin, wherein the electrodes are in fluid communication with the microcapillary tube;

inserting the biosensor cassette into a measuring instrument, wherein the biosensor cassette and the measuring instrument measure glycated albumin and non-glycated albumin in the sample; and determining the ratio of glycated albumin to total albumin in the sample.

3. The method according to either of claim 1 or 2, wherein the blood sample comprises whole blood, plasma, or serum.

4. The method according to either of claim 1 or 2, wherein the measuring instrument is a reflectance spectrophotometer or fluorometer.

5. The method according to claim 2, wherein the measuring instrument is a biosensor instrument.

6. The method according to either of claims 1 or 2, wherein the anti-glycated albumin antibody is a polyclonal antibody or a monoclonal antibody.

7. The method according to claim 6, wherein the anti-glycated albumin antibody is selected from the group consisting of an IgG purified fraction of antiserum, a purified antibody, and a binding fragment (Fab or $Fab_2$) of the antibody.

8. The method according to either of claims 1 or 2, wherein the anti-albumin antibody is a polyclonal antibody or a monoclonal antibody.

9. The method according to claim 8, wherein the anti-albumin antibody is selected from the group consisting of an IgG purified fraction of antiserum, a purified antibody, and a binding fragment (Fab or $Fab_2$) of the antibody.

10. The method according to either of claim 1 or 2, wherein the measuring instrument comprises:
 a first means for measuring glycated albumin;
 a second means for measuring non-glycated albumin;
 an internal computer chip for measurement and calculation;
 a liquid crystal display;
 a external port to transfer data to an external computer and/or printer;
 a battery and/or an external power source; and
 a rigid external case with an aperture for inserting the biosensor cassette or the test strip.

11. The method according to either of claim 1 or 2, wherein more than one blood sample from the patient is obtained over a period of time to determine the percent glycated albumin over time.

* * * * *